US007401920B1

United States Patent
Kranz et al.

(10) Patent No.: US 7,401,920 B1
(45) Date of Patent: Jul. 22, 2008

(54) HEAD MOUNTED EYE TRACKING AND DISPLAY SYSTEM

(75) Inventors: Yaron Kranz, Haifa (IL); Yoav Ophir, Zichron Yaacov (IL); Hanan Shamir, Haifa (IL); Yosi Yaeli, Haifa (IL)

(73) Assignee: Elbit Systems Ltd., Haifa (IL)

( * ) Notice: Subject to any disclaimer, the term of this patent is extended or adjusted under 35 U.S.C. 154(b) by 513 days.

(21) Appl. No.: 10/848,824

(22) Filed: May 19, 2004

Related U.S. Application Data

(60) Provisional application No. 60/472,074, filed on May 20, 2003.

(51) Int. Cl.
*A61B 3/14* (2006.01)
*G06K 9/00* (2006.01)

(52) U.S. Cl. .................. 351/210; 351/209; 351/221; 382/103; 382/117

(58) Field of Classification Search ............. 351/206, 351/209, 210
See application file for complete search history.

(56) References Cited

U.S. PATENT DOCUMENTS

| | | | |
|---|---|---|---|
| 5,331,149 A | 7/1994 | Spitzer et al. ............... 250/221 |
| 5,491,532 A * | 2/1996 | Suzuki et al. ................. 396/51 |
| 5,526,089 A * | 6/1996 | Sato et al. ..................... 396/51 |
| 5,583,795 A | 12/1996 | Smyth ................. 364/516.444 |
| 5,689,619 A | 11/1997 | Smyth .......................... 395/10 |
| 5,889,577 A * | 3/1999 | Kohayakawa ................ 351/211 |
| 6,120,461 A | 9/2000 | Smyth ......................... 600/558 |
| 6,140,980 A | 10/2000 | Spitzer et al. .................. 345/8 |
| 6,158,866 A | 12/2000 | Gulli et al. .................... 351/221 |
| 6,381,339 B1 | 4/2002 | Brown et al. ................. 382/100 |
| 6,396,461 B1 | 5/2002 | Lewis et al. ..................... 345/7 |
| 6,433,760 B1 | 8/2002 | Vaissie et al. ................... 345/8 |
| 6,507,702 B2 * | 1/2003 | Ohtani .......................... 396/50 |
| 6,636,185 B1 | 10/2003 | Spitzer et al. .................. 345/8 |
| 6,667,694 B2 | 12/2003 | Ben-Ari et al. ............. 340/980 |
| 2003/0098954 A1 * | 5/2003 | Amir et al. .................... 351/210 |
| 2004/0252277 A1 * | 12/2004 | Chmielewski et al. ....... 351/209 |
| 2006/0238877 A1 * | 10/2006 | Ashkenazi et al. .......... 359/630 |

FOREIGN PATENT DOCUMENTS

JP 2001-61785 * 3/2001

* cited by examiner

*Primary Examiner*—Jordan M Schwartz
(74) *Attorney, Agent, or Firm*—Steven M. Jensen; Edwards Angell Palmer & Dodge LLP

(57) ABSTRACT

A system for eye tracking that determines the line of sight of a user according to the relative position between the center of the pupil and a reference point, the system including an image detector that captures an image of the eye, a pupil-illuminating light source that illuminates the pupil of the user, a reference light source that illuminates a different portion of the face of the user as a reference point and an imaging processor that analyzes the captured eye image to determine the line of sight.

53 Claims, 9 Drawing Sheets

HEAD MOUNTED EYE TRACKING AND DISPLAY SYSTEM

CROSS-REFERENCE TO RELATED APPLICATIONS

This application claims the benefit under 35 U.S.C. § 119 (e) of U.S. Provisional Application No. 60/472,074, filed May 20, 2003, the entire contents of which are hereby incorporated by reference.

FIELD OF THE DISCLOSED TECHNIQUE

The disclosed technique relates to head mounted systems, in general, and to a method and system which tracks an eye of a user, while projecting images toward the eye, in particular.

BACKGROUND OF THE DISCLOSED TECHNIQUE

System and methods for eye tracking are known in the art. U.S. Pat. No. 5,583,795 to Smyth entitled "Apparatus for Measuring Eye Gaze and Fixation Duration, and Method Therefore", is directed to a device and method for measuring eye gaze and fixation duration. An electronic video display array provides controlled illumination of the eye of a user. The initial flares in display pixel brightness, generated during the electronic refresh sweep of the display, creates a sequence of point light sources. The reflections from the cornea and internal eye components reach the array of light sensors through display optics. The sensor system comprises an array of phototransistors (amplifiers), comparators, and an encoder and latch, for isolating the transistor with maximal response to the corneal reflex from the instantaneously excited light source. The corresponding video display pixel element is determined by the display refresh order, indexed by the raster scan clock pulse count. This encoded address is written by the processor onto digital memory, eventually creating a table of array matrix address for phototransistor sensor and light source pairings, accessible by digital computer routines.

The digital computer runs several routines to compute: visual line of sight, workspace line of sight, fixation status, and gaze point for each eye. The visual line of sight routine generates a three dimensional model of the eye. Utilizing the stored reflection data, the routine obtains the corneal surface reflection points, the corneal center and the pupil center, for computing of the optical origin and axis. The routine then smoothes reflection point locations using a clustering algorithm, and analyzes this data to determine the median axes. Finally, the routine computes the viewing origin and axis from the optical and median axes.

U.S. Pat. No. 6,120,461 to Smyth entitled "Apparatus for Tracking the Human Eye with a Retinal Scanning Display, and Method Therefore", is directed to a device and method for measuring eye gaze and fixation duration, wherein a retinal scanning display creates sequential sources of light. The directed light sweeps the retina in discrete steps, illuminating adjacent portions of the retina in a point-wise manner and creating a succession of reflection points. The reflections are detected by an active-pixel image sensor array composed of CMOS substrate. The sensor is integrated with a comparator array and an element address encoder and latch, both clocked by the raster scan pulse of the display driver. This determines the sensor element reaching maximum intensity or activated from a particular sequential light source reflection off the cornea. Over a refresh cycle, the corneal surface is mapped to a data table through pairings of sensor activations and corneal reflections. A CCD device (or alternatively a memory cache) is activated by the sensor array to record diffused reflections, or sensor pixels with intensities less than that of the direct reflections, as determined by the comparator array. These parameters are also used in subsequent data analysis.

After each cycle, the image processor, comprised of a stack of VLSI circuit arrays, generates a three dimensional image of the human eye, expanded to include more features and inner structures of the eye. The image processor computes a model of the cornea and optical locations for isolated image features. The optical origin and the optical and median axes are computed from internal eye features, including corneal optic center and axes, corneal surface center and axes, pupil optic center, pupil image orientation, capillary network of retinal fundus and iris pattern. The viewing origin and axis is obtained from the optical origin and axis and median axes.

U.S. Pat. No. 5,331,149 to Spitzer et al, entitled "Eye tracking system having an array of photodetectors aligned respectively with an array of pixels", is directed to an eye tracking apparatus. A flat panel display projects an image, through a photodetector array and onto a viewing screen, which is viewed by the user. Each pixel in the display is aligned with a corresponding photodetector. The light rays which are reflected from a display pixel to the fovea of the eye, are reflected back from the eye along the same optical path. The photodetector identifies the pixel from which the light ray emanated by generating a voltage signal in the array unit nearest the returned light ray. The corresponding portion of the display represents the line of sight of the user. A cursor is projected on the screen at the line of sight location to provide feedback.

In order to prevent interference from outside light, a bandpass filter, placed over the array, blocks out all wavelengths but that of the cursor. A corresponding band rejection filter is placed on the outside of the viewing screen. Alternatively, a pair of polarizers may be used instead of filters. A light polarizer is placed over the detector array, in conjunction with a ninety degree-crossed polarizer over the viewing screen. Further alternatives include using infrared light from the display, or blinking the cursor image allowing the computer to eliminate background light.

U.S. Pat. No. 6,433,760 to Vaissie et al. entitled "Head Mounted Display with Eye tracking Compatibility", is directed to a display and eye tracking system. The system includes a CCD camera, an LCD, a computer, an imaging system, at least one LED, a hot mirror and a cold mirror.

The LEDs emit 900 nm light. One of the mirrors reflects the light onto the cornea of the eye. The reflected infra-red beam from the cornea of the eye strikes the hot mirror. The hot mirror directs the reflected infra-red beam through the imaging system. The beam then passes through the cold mirror and is focused onto the CCD camera. The computer processes the beam to determine the sight direction of the user.

The LCD screen receives visual information from the computer. The imaging system displays the images from the LCD screen. The hot mirror reflects the rays from the LCD screen onto the cornea.

U.S. Pat. No. 6,396,461 to Lewis et al. entitled "Personal Display with Vision Tracking", is directed to a display apparatus. The apparatus includes control electronics, a light source, a scanning assembly and imaging optics. The imaging optics is formed from curved, partially transmissive mirrors. The mirrors receive light from a background and from the scanning assembly. The mirrors combine the light received from these sources to produce a combined image to the eye of a viewer.

The imaging optics redirects and magnifies scanned light from the scanning assembly toward the eye. The scanned light passes through the pupil of the eye, and strikes the retina of the eye to produce a virtual image. Background light passes through the mirrors and the pupil to the retina of the user, to produce a "real" image.

The apparatus further includes an infrared light source, positioned adjacent to the light source, and an optical detector. A common substrate carries the infrared light source and the light source. The imaging optics receives a locator beam from the infrared light source. The imaging optics redirect light, reflected from the eye, toward the optical detector. The detector data are input to an electronic controller. The controller accesses a look up table in a memory device to retrieve positioning data indicating a correction for the light source. The controller activates X and Y drivers to provide voltages to respective piezoelectric positioners, coupled to the substrate, for correcting the positions of the light sources.

U.S. Pat. No. 6,381,339 to Brown et al. entitled "Image System Evaluation Method and Apparatus Using Eye Motion Tracking", is directed to an eye tracking apparatus for evaluating different image systems.

The eye tracking apparatus consists of a video-based, infrared illuminated, headband mounted eye tracking technique. A collimated diode emitting infrared light illuminates the eye. A monochrome CCD camera is aligned coaxially with the diode. The camera captures "bright-pupil" reflection from the retina of the subject and the first surface reflection of the cornea ("first Purkinje image"). An eye tracker control unit digitizes the camera images and thresholds the image at two levels in real-time.

The first threshold level isolates pixels within the bright pupil, and the second threshold level isolates those pixels that are within the corneal reflection.

A lab computer then computes the centroid of the pupil and the first Purkinje image. The eye-in-head position is calculated based on the relative location of the two centroids when both items are available in the camera image, in order to make the system less sensitive to movement of the tracker with respect to the head.

A magnetic field head tracker monitors head position and orientation in real time. The head tracker comprises a transmitter unit mounted above the head of the subject, which contains three orthogonal coils that are energized in turn. A receiver unit contains three orthogonal antennae coils that pick up the corresponding signals from the transmitter. The head position and orientation points are determined from the absolute and relative strengths of the transmitter/receiver coil pairs.

The gaze position is then calculated, using eye-in-head and head position/orientation data, in the form of the intersection of the line-of-sight with the working plane. The eye tracking apparatus provides a digital data stream containing eye-in-head, head orientation and position, and gaze intercept information. In addition a camera present on the headband provides a video record of the scene from the perspective of the subject, also indicating the same positional data.

U.S. Pat. No. 6,158,866 to Gulli et al. entitled "Optical System Combining Image Presentation and Eye Analysis", is directed to an image presentation system. The image presentation portion of the system comprises an image generator and an optical transmission channel. The image generator sends images to a display screen. An optical transmission channel passes the images from the display to the eye of the use. The channel includes a collimating device that projects the screen image to be perceived by the user as located at an infinite distance, or at a finite distance if desired. The channel also includes a combiner allowing the user to perceive a superimposed image in visible light.

The eye tracking portion comprises an illuminating system and image detection system. The illuminating system consists of a light source and optical transmitter which illuminates the retina at the rear inner surface of the eye of the user. The illuminating light wave propagates through a bundle of optical fibers before reaching the eye. A scanning system at the light source allows for selective illumination of different fiber groups and scans the retina. The reflected light follows the inverse path of the illuminating light, passing through the optical fibers to the scanning system. A semi-reflecting mirror reflects the light to the image detection system. The image detection system consists of a detector that detects the intensity of reflected light, and a device that generates a retinal image of the eye.

Conventional helmet mounted display systems use the line of sight of the helmet in order to aim at a target. Such systems utilize a position and orientation sensor, mounted on the helmet, in order to define the helmet line of sight. Thus, a pilot needs to move his head and helmet (i.e., using the neck), in order to aim at a target.

U.S. Pat. No. 6,667,694 B2 issued to Ben-Ari et al., and entitled "Gaze-Actuated Information System" is directed to a gaze-actuated information system for generating an audio output for a pilot of an aircraft, according to an eye gaze direction of the pilot and a reference direction. The gaze-actuated information system includes a helmet mounted system, a cockpit mounted system, a weapon system unit and a weapon system.

The helmet mounted system includes an eye tracking system, a transmitter and a first power supply. The cockpit mounted system includes a first transceiver, a processor, an audio system, a helmet position system and a second power supply. The weapon system unit includes a second transceiver, a control interface and a third power supply. The weapon system includes a seeker and a launcher. The processor includes a direction correlation system. The eye tracking system, the transmitter, the first power supply, the first transceiver, the processor and the helmet position system form a gaze-direction determining system.

The eye tracking system derives the eye gaze direction of an eye of the pilot relative to a helmet of the pilot. The helmet position system derives the position of the helmet within a cockpit of the aircraft. The processor derives the eye gaze direction of the eye of the pilot relative to a frame of reference moving with the cockpit, according to the eye gaze direction relative to the helmet, and according to the position of the helmet. The weapon system unit relays seeker direction information from the weapon system to the cockpit mounted system.

When the pilot looks at a target, the seeker is locked to the eye gaze direction of the pilot. The pilot brings the seeker into alignment with the target by looking toward the target, and designates the target by depressing a control button. Depressing the control button releases the seeker from the eye gaze direction, and allows the seeker to track the target. At this stage the audio system generates a first audible signal to indicate to the pilot that the seeker has locked on to the target. Before firing a missile toward the target, the pilot verifies that the seeker has locked on to the correct target.

For performing this verification, the direction correlation system compares the eye gaze direction relative to the frame of reference with the target direction relative to the frame of reference. If the eye gaze direction and the target direction are equal within a given degree of accuracy, then the direction correlation system determines that the pilot is currently looking at the target which is being tracked, and the audio system generates a predefined audible signal.

The direction correlation system compares the eye gaze direction relative to the frame of reference with a reference direction relative to the frame of reference. The reference direction is chosen to correspond to a region of the field of view of the pilot, with which certain information is associated. If the eye gaze direction and the reference direction are equal within a given degree of accuracy, then the audio system generates audio output to the pilot indicative of the information associated with that reference direction.

SUMMARY OF THE DISCLOSED TECHNIQUE

It is an object of the disclosed technique to provide a novel method and system for tracking the eye of a user. The disclosed technique overcomes the disadvantages of the prior art by providing an eye tracking system for determining the line of sight of a user, based on the position of the center of the pupil with respect to at least one reference region on the face of the user. The system may utilize this information to allow the user to select and initiate actions in an extremely rapid period of time and simultaneously serve as real-time monitoring of user situational awareness. A particular useful application for the system is for auxiliary machine (e.g. weapon) control in armed vehicles.

In accordance with the disclosed technique, there is thus provided an eye tracking system, having at least an image detector, a pupil-illuminating light source, an at least one reference illuminating light source and an imaging processor. The image detector captures an image of the eye of the user. The pupil-illuminating light source illuminates the pupil of the eye of the user. The reference light source illuminates a different portion of the face of the user as a reference point. This reference point may be the cornea or the eyelids. The imaging processor analyzes the captured eye image to determine the line of sight of the user according to the relative position between the center of the pupil and a reference point. Additional facial features of the user, such as the shape of the pupil, may also be used in determining the line of sight. The system may include an ambient light detector that detects the intensity of the ambient light and adjusts the respective light beams accordingly. The system may include a display module that displays an image to the user. The image displayed to the user may be controlled according to the detected line of sight. In particular, the user can select a display element, representing an action to undertake (select a missile, lock onto target, and the like), by gazing at the appropriate display element sufficiently. According to an aspect of the disclosed technique, the system is mounted on a helmet. A helmet visor is included in the system, which reflects light from the respective light beams toward the eye of the user while allowing the user to view an external scene without disruption.

According to the disclosed technique there is also provided a method for tracking the eye of a user by determining the line of sight according to the pupil region and at least one reference region, as indicated in a captured image of the eye of the user. The illuminating light source may be controlled according to the intensity of the detected ambient light. The image of the eye may also be analyzed to determine a physiological state of the user, and initiate a warning signal if necessary. A display image, that may include elements representing actions to be selected, may be controlled according to the line of sight of the user.

BRIEF DESCRIPTION OF THE DRAWINGS

The disclosed technique will be understood and appreciated more fully from the following detailed description taken in conjunction with the drawings in which.

DETAILED DESCRIPTION OF PREFERRED EMBODIMENTS

Figure 1:
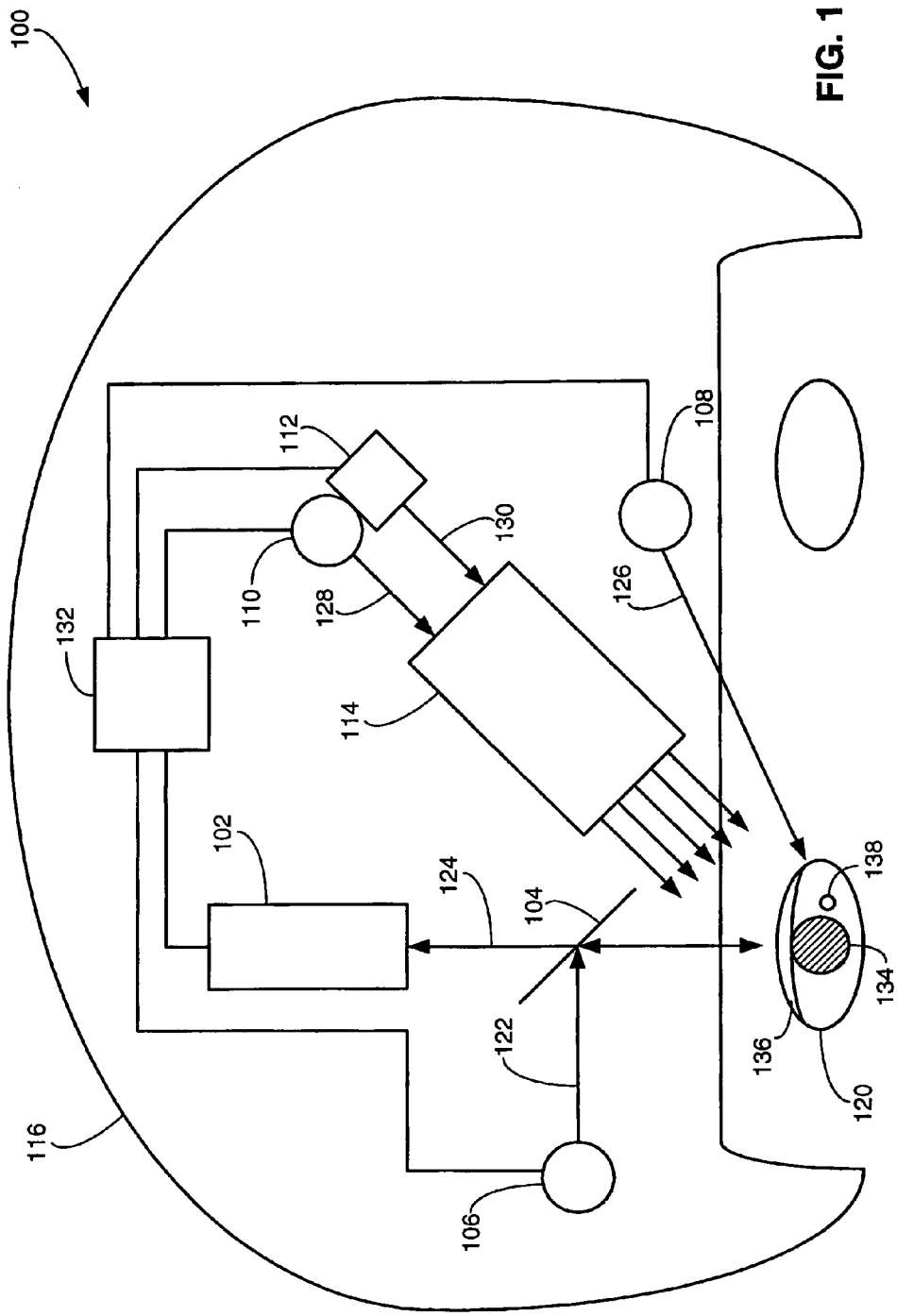
FIG. 1 is a schematic front-view illustration of a system, constructed and operative in accordance with an embodiment of the disclosed technique, which displays images to an eye of a user and which further tracks the eye.

The disclosed technique overcomes the disadvantages of the prior art by providing a head-mounted system which tracks an eye of a user, while projecting images toward the eye. Reference is now made to FIG. 1, which is a schematic front-view illustration of a system 100, constructed and operative in accordance with an embodiment of the disclosed technique, which displays images to an eye 120 of a user and which further tracks eye 120. A pupil 134 is located within eye 120. System 100 (e.g., eye tracker 534 illustrated herein below in FIG. 6) includes a camera module 102, an imaging processor 132, a beam splitter 104, light sources 106, 108 and 110, a display module 112 and a collimating optical assembly 114, all mounted on a helmet 116.

Beam splitter 104 transmits a portion of light incident there-upon, and reflects another portion of the incident light. For example, beam splitter 104 may be a polarizing beam splitter (PBS). Light sources 106, 108 and 110 emit non-visible light. For example, each of light sources 106, 108 and 110 may emit infra-red (IR) light or near-infra-red (NIR) light. Light sources 106, 108 and 110 may be light-emitting diodes (LEDs), NIR-filtered broadband light sources, and the like.

Display module 112 produces an image to be viewed by the user (e.g., display module 112 may include a cathode ray tube (CRT), a rear illuminated liquid crystal display (LCD), or an organic light emitted diode (OLED)). Light source 110 and display 112 are coupled with collimating optical assembly 114.

Camera module 102 receives an image, which passes through beam splitter 104. Camera module 102 includes an image sensor such as a charge-coupled device (CCD), complementary metal oxide semiconductor (CMOS), and the like, for detecting images.

Imaging processor 132 is coupled with camera module 102, display module 112 and with light sources 106, 108 and 110. In the present example, imaging processor 132 is mounted on the helmet 116. It is noted, however, that the processor may generally be on-helmet, off-helmet, or partially on-helmet (e.g., when the processor consists of a chipset).

Imaging processor 132 receives image data from camera 102, and determines the visual line of sight of the eye 120 according to these image data. Imaging processor 132 may further record images, communicate with an external source (e.g., a user interface, an ambient light detector), and control the display 112 and the light sources 106, 108 and 110.

In the present example, light sources 106, 108 and 110 emit light substantially in the same predetermined range of wavelengths. The camera module 102 further includes a filter (not shown), which admits light in the same range of wavelengths as light sources 106, 108 and 110, and which filters out light which is outside of this range. It is noted, however, that the light sources may generally emit light having different ranges of wavelengths, and the camera may have various detection spectrums. The general requirement in order for the camera to detect the reflections of light originating from light sources 106, 108 and 110, is that the combined emission spectrum of light sources 106, 108 and 110, has a substantial overlap with detection range of camera module 102.

Light source 106 emits a non-visible illuminating light beam 122 towards beam splitter 104. Beam splitter 104 partially reflects light beam 122 toward the eye 120, thereby illuminating the eye 120. Illuminating light beam 122 is concentric with the optical axis of the camera module 102. A portion of illuminating light beam 122 is reflected back from the pupil 134 of the eye 120, as a light beam 124, to the image sensor of camera module 102. Thus, pupil 134 appears as a bright spot in the image detected by camera module 102. Accordingly, imaging processor 132 determines the position of the center of pupil 134.

According to another embodiment of the disclosed technique, imaging processor 132 is further coupled with an ambient light detector (not shown), which can be on-helmet or off-helmet. It is noted that under certain conditions, camera module 102 may not be able to detect pupil 134 as a bright spot. For example, ambient light in the system 100 may reach high levels of intensity. Since viewing the pupil 134 requires a minimal contrast level between the pupil and its surrounding non-transparent tissue (i.e., the iris), the intensity level of light beam 122 must also increase as the intensity of the ambient light increases. However, the intensity of light beam 122 may be limited by a safety threshold.

If the intensity of light beam 122, which would be required for viewing the pupil 134 as a bright spot, is beyond the safety threshold, the ambient light detector can signal to imaging processor 132 accordingly. Imaging processor instructs light sources 106, 108 and 110 to illuminate the eye differently. For example, light source 106 may significantly reduce the intensity of light beam 122. Thus, pupil 134 shall appear in the image detected by camera module 102, as a dark spot. Imaging processor 132 then detects pupil 134 according to different criteria. For example, the criterion for detecting a "bright pupil" may select image portions which are beyond a certain brightness threshold, while the criterion for detecting a "dark pupil" may select image portions beneath a "darkness" threshold.

Light source 110 emits a non-visible illuminating light beam 128 toward collimating optical assembly 114. Display module 112 emits a light beam 130, which carries a visible image, toward collimating optical assembly 114. Collimating optical assembly 114 collimates light beams 128 and 130, and directs the collimated light beams toward the eye 120 of the user. Imaging processor 132 detects the corneal reflection 138 of light beam 128 (i.e., corneal reflection 138 is the reflection of light beam 128 from the cornea of the eye 120). Since light beam 128 is collimated, the position of corneal reflection 138 on the cornea is invariant to the movement of the eye 120, relative to the light source 110 position (e.g., such relative movement can occur under helmet slippage). In the present example, corneal reflection 138 is located outside of the area of pupil 134. It is noted, however, that corneal reflection 138 may, in general, partially or completely overlap with the area of pupil 134. It is further noted that the position of the corneal reflection 138 depends on the gaze of the eye 120.

Light source 108 emits a non-visible illuminating light beam 126 toward the eye 120 and eyelids 136 of the user. A portion of light beam 128 (not shown) is reflected toward the camera module 102. Thus, camera module 102 detects an image of the eye 120 and eyelids 136 of the user. Light source 108 may be configured to produce flood illumination over certain areas of the face (e.g., eyes and eyelids) with homogeneous light (i.e., intensity, polarization, wavelength and the like). For example, a diffuser may be used to generate a uniform intensity of illumination.

According to a further embodiment of the disclosed technique, the imaging processor 132 determines the line of sight of the user according to the relative position between pupil 134 and the corneal reflection 138. Imaging processor 132 may further use the shape of pupil 134 in the process of determining the line of sight. For example, imaging processor 132 can extract from the eye image the position of the center of pupil 134 and the center of corneal reflection 138. Thus, the imaging processor can calculate the relative position between the center of the pupil and the center of the corneal reflection. Moreover, the imaging computer may further calculate and analyze the shape of the pupil. The imaging processor 132 may then transform these results, using a predetermined model transformation, to determine the line of sight of the user. It is noted that the model transformation is based on knowledge of the physiology of the eye, and may further be determined according to previously acquired data regarding the user. The position of the eyelids 136 may be used in order to enhance the accuracy of the calculation of the line of sight. For example, either corner of the eyelids is generally at rest relative to the face of the user. Thus, a corner of the eyelids 136 may be used as a further reference point, in addition to the pupil and the corneal reflection.

Alternatively, the position of eyelids 136 may be used for calculating the line of sight of the user, in case one of the other reference points (i.e., the pupil 134 or the corneal reflection 138) is not available. For example, under certain conditions, the corneal reflection 138 may not be available. Accordingly, the imaging processor determines the line of sight according to the relative position between the center of the pupil 134 and a corner of the eyelids 136.

Furthermore, imaging processor 132 may analyze changes over time of features of the eye in the process of determining the line of sight of the user. Imaging processor 132 thereby determines temporal features of the eye. Such analysis may include shape variations of different parts of the eye, movement profiles of different eye features as they change over time, including associated velocity and acceleration vectors, and the like. Such analysis may involve statistical analysis, peak analysis, and the like. As well, such analysis may be compared with respective features associated with a reference eye model, thereby detecting anomalies in the eye. It is noted that the imaging processor may calculate the line of sight dynamically. Accordingly, the imaging processor 132 initially calculates the line of sight, and then associates any subsequent movement in the eye with a change of the line of sight.

According to another embodiment of the disclosed technique, imaging processor 132 determines the physiological state of the user according to the position and movement of either eyelids 136 or pupil 134. For example, the position of eyelids 136 and the movement of pupil 134, can indicate the fatigue state of the user, and identify loss of consciousness (LOC), and the like. For example, the imaging processor can thus identify a loss of consciousness under high G loads (G-LOC). This physiological state can be for example, fatigue, loss of consciousness, cross-eye, astigmatism, eye damage, vertigo, and the like.

When certain physiological conditions are detected, imaging processor 132 can initiate a response accordingly. For example, when imaging processor detects that the user is sleepy, imaging processor can instruct an alarm system to sound an audible alarm, to generate a mild electric shock, alert the attention of a command center, and the like.

System 100 further includes a semi-transparent visor or combiner (not shown). It is noted that the paths of the light beams traveling between the eye 120 and the elements of system 100 are shown only schematically in FIG. 1. Light beams 122, 124, 126, 128 and 130 are actually reflected from the visor before reaching the eye 120 or the camera module 102.

Figure 2:
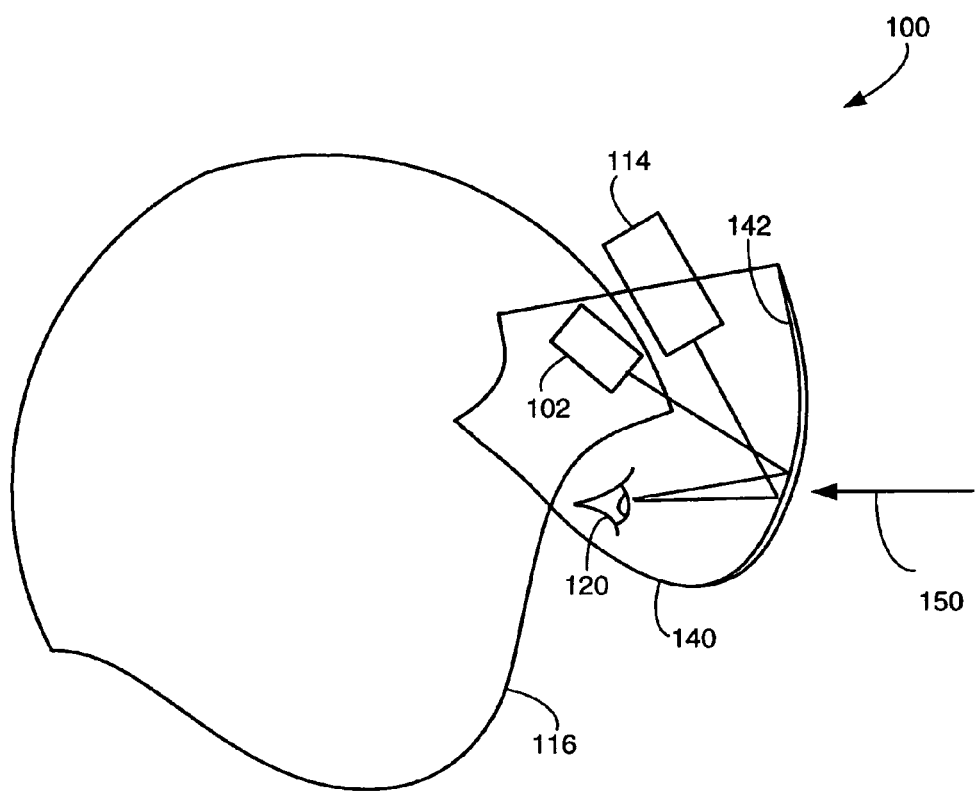
FIG. 2 is a schematic side view illustration of the system of FIG. 1.

Reference is now made to FIG. 2, which is a schematic side-view illustration of system 100 (FIG. 1). A visor 140 reflects light beams passing between the eye 120 and the camera 102 (i.e., light beam 124 of FIG. 1), as well as light beams passing between the collimator 114 and the eye 120 (i.e., light beams 128 and 130 of FIG. 1). In the present example, the surface of visor 140 is spherical. It is noted, however that the surface of visor 140 may have various shapes such as spherical, aspherical, planar, and the like. It is further noted that a spherical visor may have some degree of rotational freedom, without affecting the paths of light beams reflected there from.

Visor 140 at least partially transmits visible light, thereby enabling the user to view a scene there through. Visor 140 may further filter out light having substantially the same wavelengths as illuminating light beams 122, 126 and 128. For example, the visor may include a pigment which absorbs light having these wavelengths. Thus, visor 140 significantly reduces light having these wavelengths passing entering the space between the visor and the face of the user. This substantially eliminates interference to the system 100 caused by ambient light (e.g., light from the sun), which is generally referenced 150.

Visor 140 is coated with an inner coating 142. It is noted that coating 142 may coat the entire inner side of visor 140. For example, inner coating 142 may be an interference mirror coating, which has peak reflection response at the wavelength region of light beams 122, 126 and 128 and display 112. Thus, inner coating 142 prevents any light having these wavelengths from traveling from the inner side of the visor (i.e., the space between the visor and the face of the user) to the outer side of the visor.

Thus, the space between the visor and the face of the user is practically optically isolated at these wavelengths. Substantially all of the light having the same wavelengths as the illuminating light beams, which is detected by camera module 102, originates only from light sources 106, 108 and 110. Thus, the signal (i.e., light that originated in one of the light sources) to noise (i.e., ambient light 150) ratio (SNR) is sufficient for analyzing the image received by camera module 102.

It is noted that a debriefing camera may be incorporated with system 100. Such a camera can provide data regarding the position and orientation of the helmet 116 during the flight. Taken together with data from camera module 102, these data may provide further insight regarding the view seen by the user. Similarly, the system may be incorporated with a position and orientation sensor mounted on the helmet 116 (e.g., head orientation tracker 536 illustrated in FIG. 6), as well as a position and orientation sensor which is associated with the aircraft (e.g., vehicle position and orientation tracker 538 illustrated in FIG. 6).

Figure 3A:
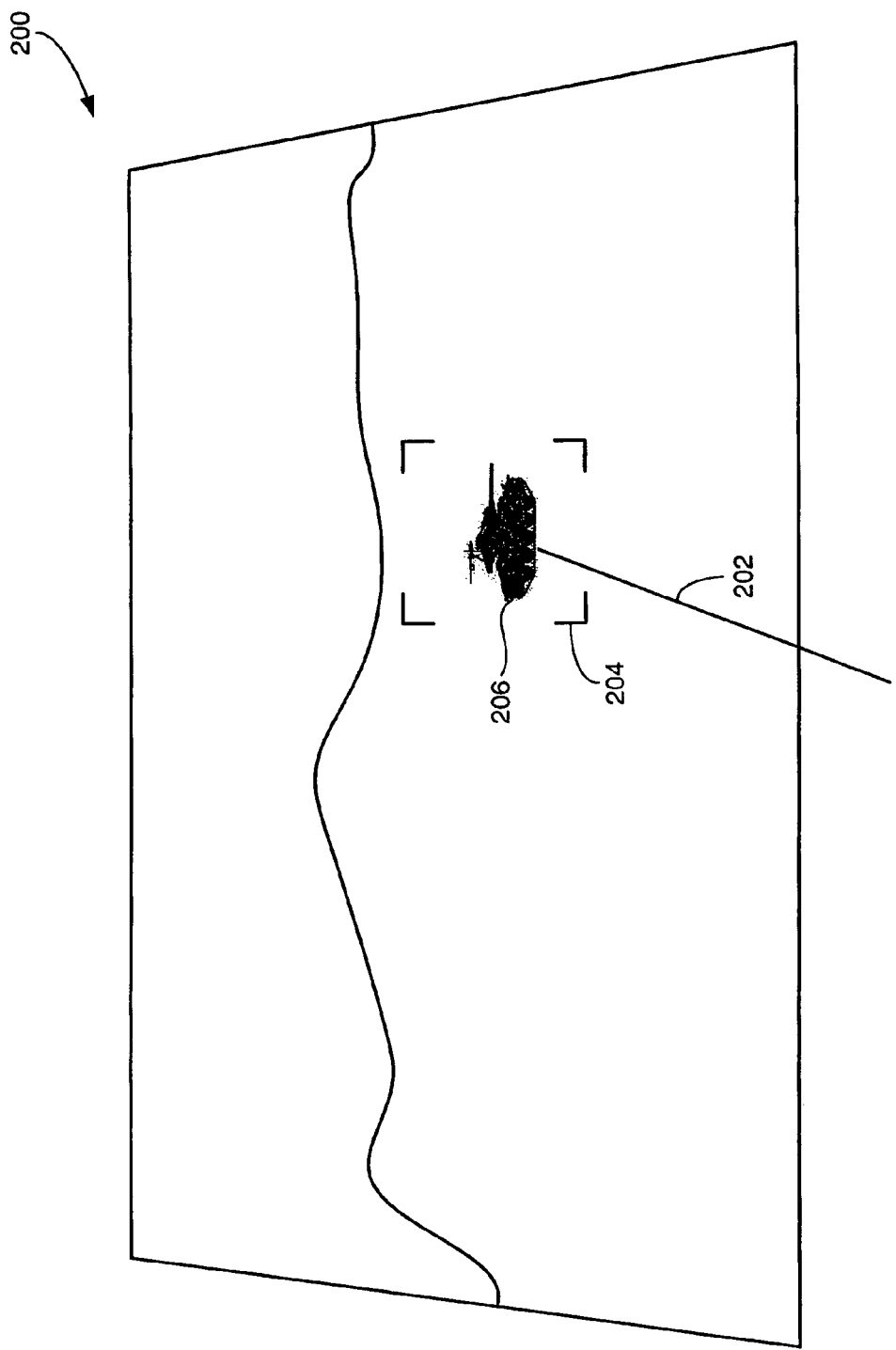
FIG. 3A is a schematic illustration of a first scene, which is viewed by a user, in accordance with another embodiment of the disclosed technique.
Figure 3B:
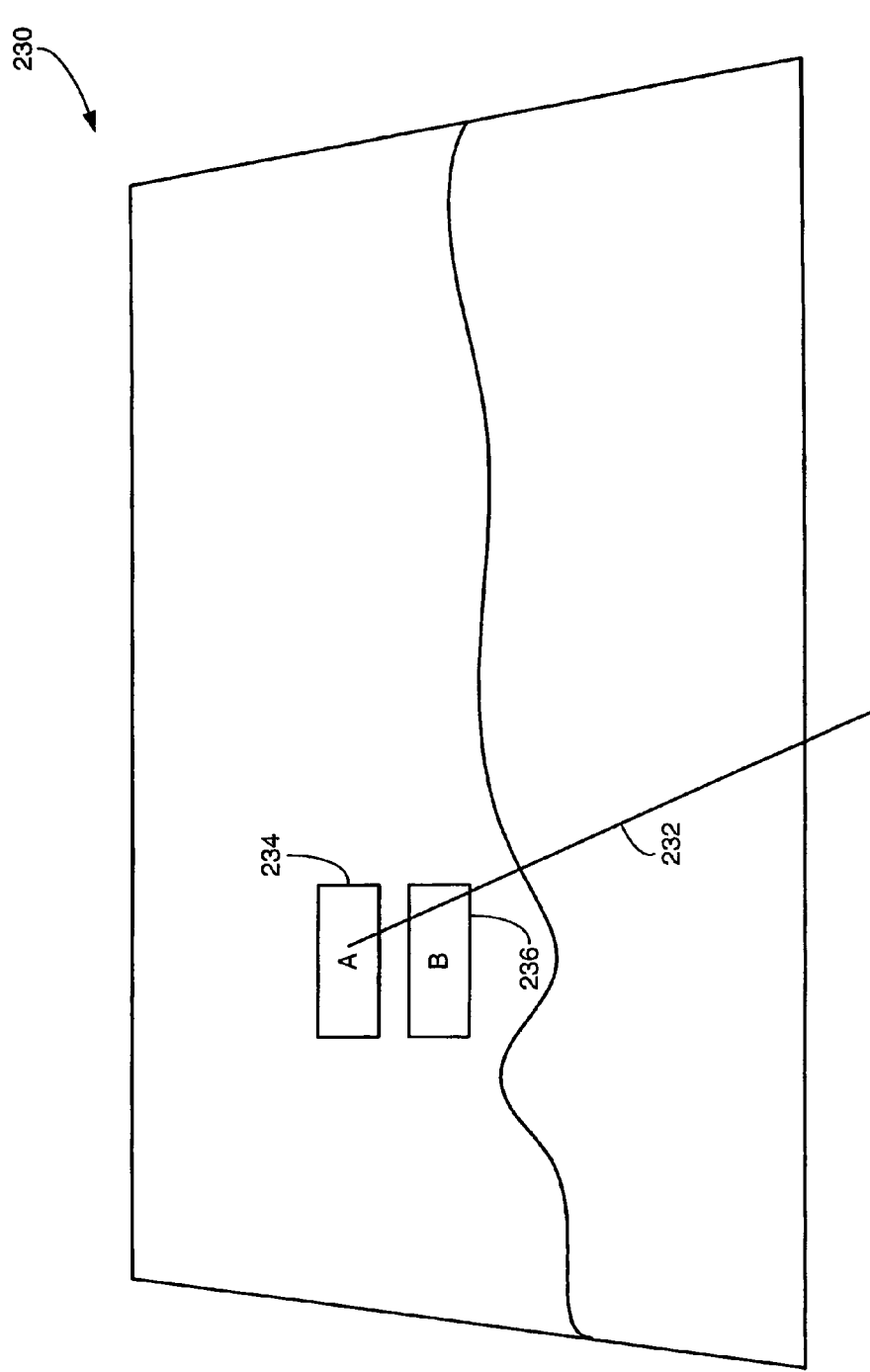
FIG. 3B is a schematic illustration of a second scene, which is viewed by the user, in accordance with a further embodiment of the disclosed technique.
Figure 3C:
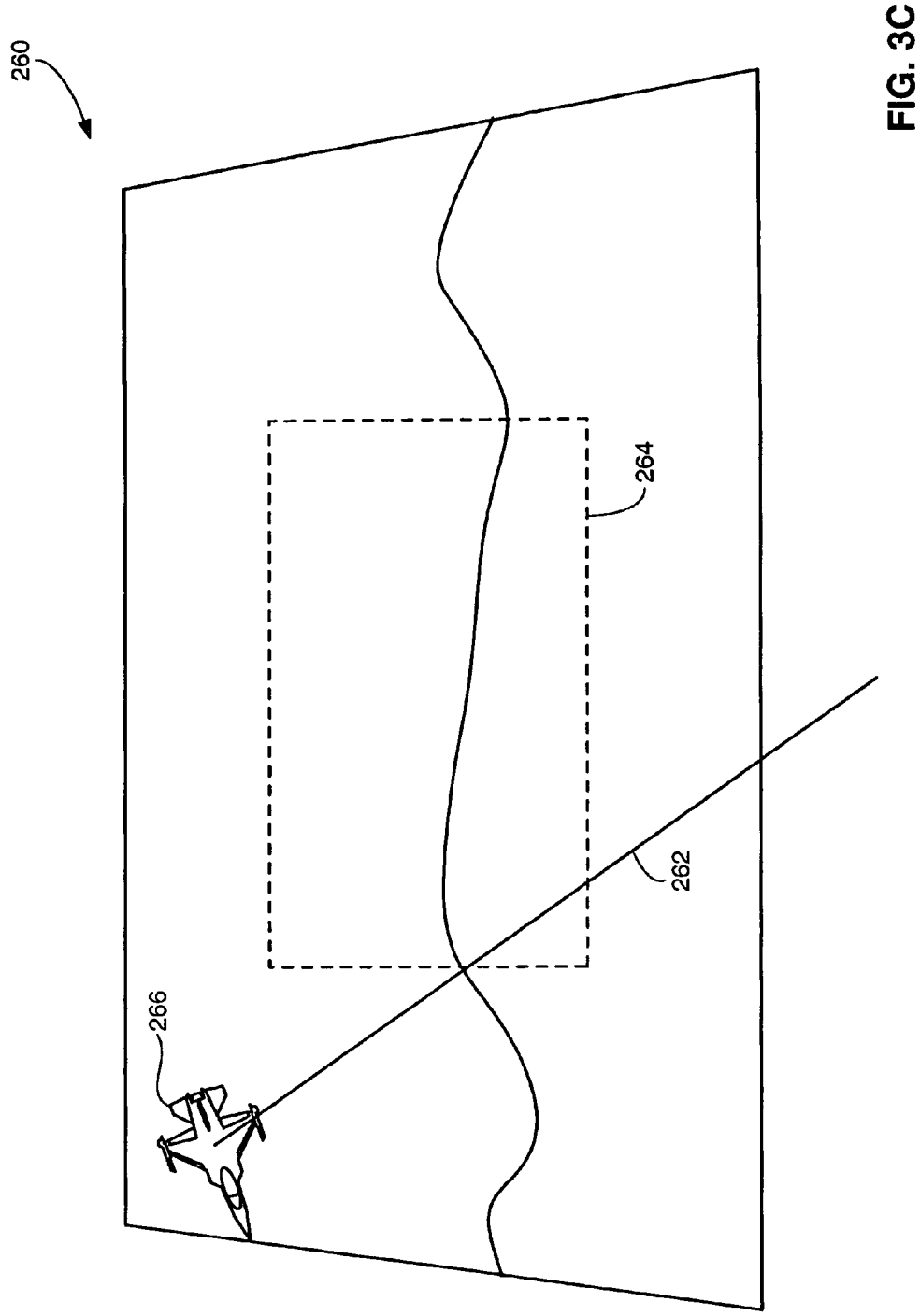
FIG. 3C is a schematic illustration of a third scene, which is viewed by the user, in accordance with another embodiment of the disclosed technique.

In accordance with another embodiment of the disclosed technique, the image displayed to the viewer is controlled according to the detected line of sight. Reference is now made to FIGS. 3A, 3B and 3C. FIG. 3A is a schematic illustration of a first scene, generally referenced 200, which is viewed by a user, in accordance with another embodiment of the disclosed technique. FIG. 3B is a schematic illustration of a second scene, generally referenced 230, which is viewed by the user, in accordance with a further embodiment of the disclosed technique. FIG. 3C is a schematic illustration of a third scene, generally referenced 260, which is viewed by the user, in accordance with another embodiment of the disclosed technique. In the examples set forth in FIGS. 3A, 3B and 3C, the user is operating an aircraft (e.g., the user is an aviation crew member). It is noted, however, that the disclosed technique may be applied to various applications for extending the user ability to interface with systems, such as in a tank, a submarine, various types of simulators, assembly lines, apparatuses for persons with disabilities, and the like.

With reference to FIG. 3A, scene 200 includes a target 206. In the example set forth in FIG. 3A, target 206 is a tank. A target marking 204 is superimposed on the scene 200. Target marking 204 is displayed around the line of sight 202 of the viewer. It is noted that the line of sight 202 is shown for purposes of explanation only and is generally not displayed to the user. The line of sight extends from the pupil, perpendicularly to the cornea and hence, from the visual perspective of the user, this virtual line is a single point located exactly at the center of the field of view of each eye.

In the present example, the user attempts to aim at target 206 and direct a weapon (e.g., weapon 532 illustrated in FIG. 6) at this target. In order to aim at the target, the user simply gazes at the target, thereby setting the line of sight 202 to the direction of the target. The system identifies the target along the determined line of sight 202. The target marking 204, displayed around the target, helps the user to determine whether the aim is sufficiently accurate. When the aim is sufficiently accurate, the user can fire at the target (e.g., by pressing a manual button, providing a vocal command). Before the weapon is actually fired, the line of sight 202 of the user is used by the weapon system for target acquisition. More specifically, in order to determine the actual targeting location at which the user is aiming, the disclosed technique implements a coordinate system hierarchy.

Accordingly, the disclosed technique cascades the pupil line of sight coordinate system (i.e., eye tracking), within the helmet line of sight coordinate system (i.e., helmet position and orientation), which is further registered with aircraft position (e.g., a global positioning system (GPS) combined with a radar) and orientation (e.g., a gyroscope-based sensor). The user may then be prompted by audible or visual means (or both) to provide confirmation of the selected target. The system receives a confirmation response from the user by similarly audible or visual means (or both). After the weapons system has completed confirmation of target acquisition, the system may then direct the weapon toward the target (after this point the weapons guidance mechanisms take over).

It is noted that the disclosed technique provides the user with a field of aim, which may include any point in the field of view of the eyes of the user. It is further noted that the speed and stability of the aim of the user are virtually limited only by the physiological limitations of the eye of the user.

It is noted that an aircraft may be subject to extreme conditions (e.g., during combat), such as a high gravitational (G) force in various directions, vibrations, pressure, and the like. The human eyes are naturally virtually self-stabilized by the vestibular ocular reflex. By constantly tracking the eye and determining the visual line of sight, the disclosed technique provides the user with stability of the aim, even when the plane is subject to such extreme conditions. Thus, the disclosed technique uses the natural self-stabilization of the eyes in order to compensate for head vibrations.

In accordance with another embodiment of the disclosed technique, the eye tracking system registers logical display elements according to the line of sight of the viewer. Thus, the user can select display elements using the eye. With reference to FIG. 3B, display elements A (referenced 234) and B (referenced 236) are superimposed on scene 230. Display elements 234 and 236 each represent an action, (e.g., selecting missiles, eject seat, transmit a distress signal, and the like), which the user can select.

The eye tracking system initially registers logical display elements with the field of view of the viewer. Thus, the system detects when the user gazes at a certain logical display element. Hence, the user can select a logical display element by gazing at this element and confirming the selection. In the present example, the user is selecting option A. The selection may be confirmed by various confirmation mechanisms, such as manual confirmation, gazing at the logical display element for a minimal duration, providing vocal indication, and the like.

In accordance with another embodiment of the disclosed technique, the user can select targets outside of the field of display. Reference is now made to FIG. 3C, which is a schematic illustration of a third scene, generally referenced 260, which is viewed by the user, in accordance with another embodiment of the disclosed technique.

Scene 260 includes a target 266. In the example set forth in FIG. 3C, target 266 is an enemy plane. The field of display of the system, referenced 264, represents the area in which the system can display images to the user. It is noted that the field of display 264 is typically smaller than the field of view of the human eye. It is further noted that the field of display 264 is shown for purposes of explanation, and does not actually appear on scene 260.

Target 266 is located outside of the field of display 264, and hence, the system does not display a target marking (e.g., similar to target marking 204 of FIG. 3A) around target 266. The user of system 100 can lock on to target 266, by directing the field of view 262 toward the target (i.e., by looking at the target), and by further activating a confirmation mechanism.

Figure 4:
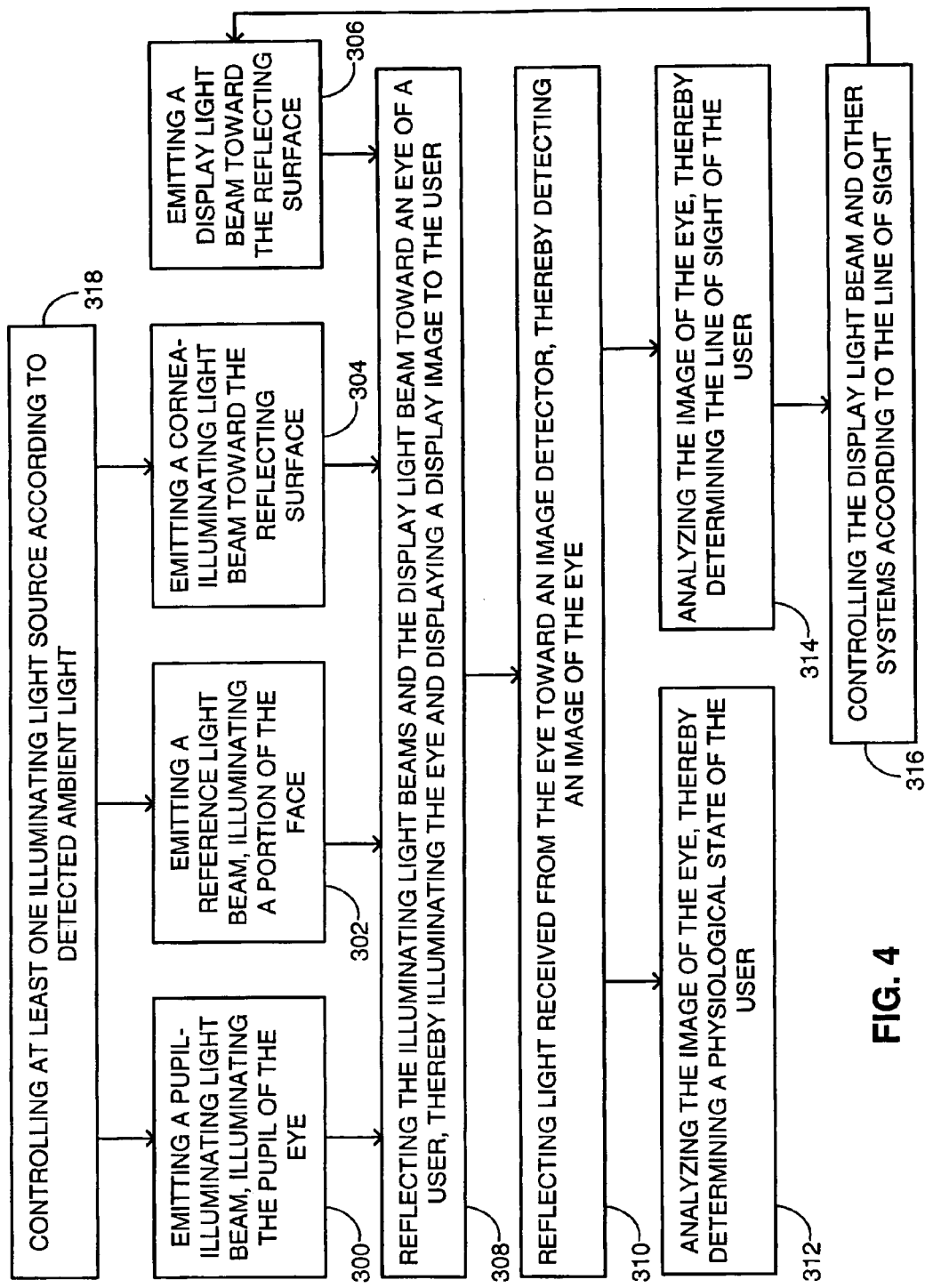
FIG. 4 is a schematic illustration of a method for projecting images toward the eye of a user while tracking the eye, operative in accordance with a further embodiment of the disclosed technique.

Reference is now made to FIG. 4, which is a schematic illustration of a method for tracking an eye of a user, while projecting images toward the eye, operative in accordance with a further embodiment of the disclosed technique. In procedure 300, a pupil-illuminating light beam is emitted toward a reflecting surface. Such a pupil-illuminating light beam is directed at illuminating a pupil and the tissue surrounding that pupil in a way which emphasizes the contrast between the pupil and that tissue. It is noted that the pupil-illuminating light beam may reach the reflecting surface indirectly. Accordingly, the light beam is first emitted toward at least one optical element, which then directs the light beam toward the reflecting surface. With reference to FIGS. 1 and 2, light source 106 emits light beam 122 toward beam splitter 104 and from there toward the inner coating 142 of the visor 140.

In procedure 302, an eyelid-illuminating light beam is emitted toward the reflecting surface. Such an eyelid-illuminating light beam is directed at illuminating the entire eye and eyelids, in a way which enables tracking the position of the eyelids. With reference to FIGS. 1 and 2, light source 108 emits light beam 126 toward the inner coating 142 of visor 140.

In procedure 304, a cornea-illuminating light beam is emitted toward the reflecting surface. Such a cornea-illuminating light beam is directed at illuminating the cornea of the eye, such that a visible point reflection appears on the cornea of the eye. With reference to FIGS. 1 and 2, light source 110 emits light beam 128, through collimating optical assembly 114, toward the inner coating 142 of visor 140.

In procedure 306, a display light beam is emitted toward the reflecting surface. The display light beam carries an image to be viewed by the user. With reference to FIGS. 1 and 2, light source 112 emits light beam 130, through collimating optical assembly 114, toward inner coating 142 of visor 140.

In procedure 308, the illuminating light beams and the display light beam are reflected toward an eye of a user, thereby illuminating the eye and displaying a display image to the user. With reference to FIGS. 1 and 2, inner coating 142 of visor 140 reflects light beams 122, 126, 128 and 130 toward the eye 120.

In procedure 310, light received from the eye is reflected toward an image detector, thereby detecting an image of the eye. With reference to FIGS. 1 and 2, inner coating 142 of visor 140 reflects portions (not shown) of light beams 122, 126 and 130, through beam splitter 104, toward camera module 102.

In procedure 312, the image of the eye is analyzed, thereby determining a physiological state of the user. With reference to FIG. 1, imaging processor 132 analyzes the image of the eye 120, and determines the fatigue state of the user according to the position and movement of the eyelids.

In procedure 314, the image of the eye is analyzed, thereby determining the line of sight of the user. With reference to FIGS. 1 and 2, imaging processor 132 analyzes the image of eye 120 received from camera module 102, and determines the line of sight of the user according to the relative position of the pupil 134, the corneal reflection 138 and the structure position of the eyelids 136.

In procedure 316, the display light beam is controlled according to the line of sight of the user. With reference to FIG. 3A, the display light source beam projects an image including target marking 204. The position of target marking 204 is controlled according to the position of the line of sight 202 of the viewer.

It is noted that other systems may be controlled according to the line of sight of the user. For example, an ejection mechanism, a firing mechanism, mode of operation, and the like, may be controlled according to the line of sight.

In procedure 318, at least one illuminating light source is controlled according to detected ambient light. In the example set forth in FIGS. 1 and 2, an ambient light detector (not shown) detects the intensity level of ambient light 150, and provides imaging processor with a signal accordingly. When the intensity levels exceed a certain threshold, imaging processor instructs light source 106 to substantially reduce (or completely eliminate) the intensity of illuminating light beam 122. It is noted that procedure 318 is performed before procedures 300, 302 and 304.

In accordance with another embodiment of the disclosed technique, the apparatus is mounted in front of the user, not being attached to the user (e.g., not being mounted on a helmet). In such a system, the module which tracks the head can be physically coupled with the head (e.g., attached to a helmet) or visually tracking the position of the head from a remote location, in the vicinity of the user.

Figure 5A:
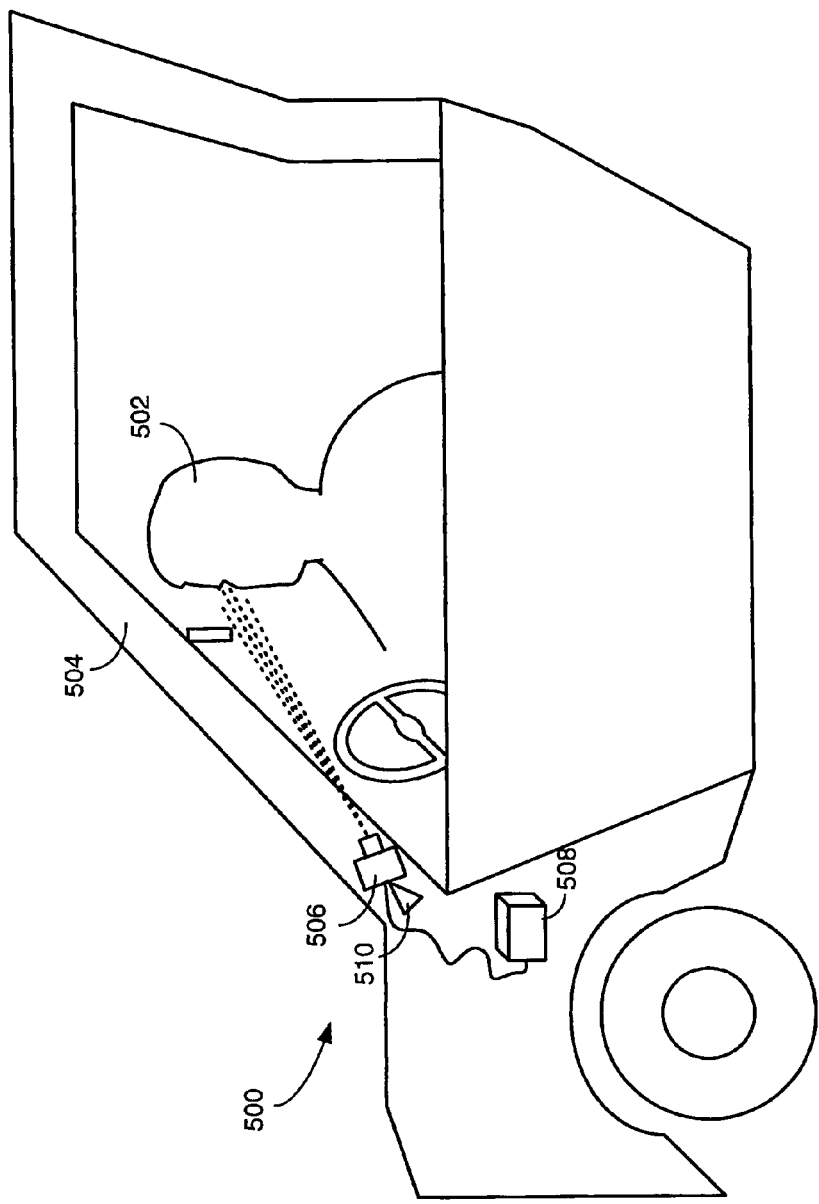
FIG. 5A is a schematic side-view illustration of a system, constructed and operative in accordance with another embodiment of the disclosed technique.
Figure 5B:
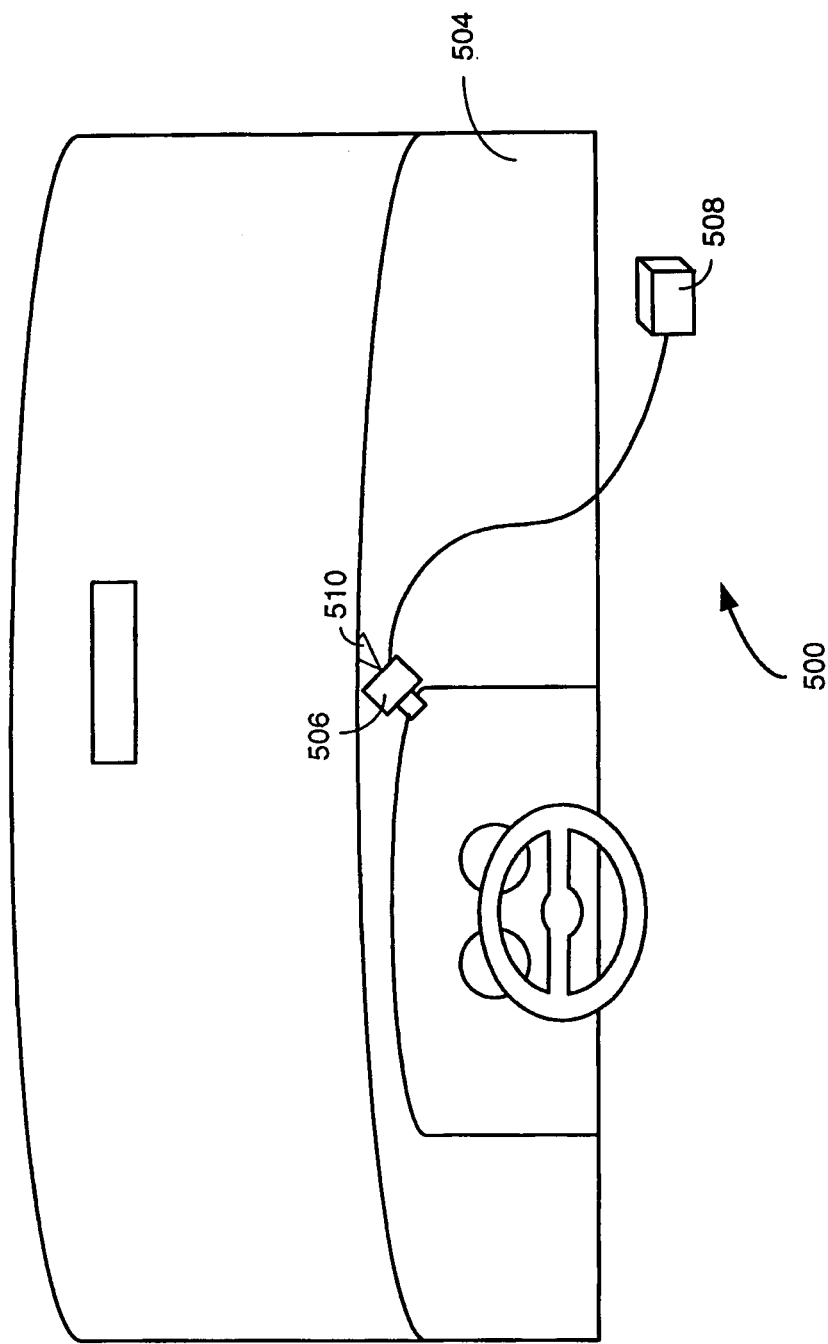
FIG. 5B is a schematic front-view illustration of the system of FIG. 5A.

Reference is now made to FIGS. 5A and 5B. FIG. 5A is a schematic side-view illustration of a system, generally referenced 500, constructed and operative in accordance with another embodiment of the disclosed technique. FIG. 5B is a front-view illustration of the system of FIG. 5A. In the examples set forth in FIGS. 5A and 5B, the user is operating a vehicle (i.e. the user is an automobile driver). It is noted that this embodiment of the disclosed technique may be applied to any type of vehicle (e.g., bus, truck, motorcycle, or bicycle), vessel (e.g., boat or submarine) or aircraft (e.g., airplane, helicopter, or spaceship) or in a stationary facility.

With reference to FIG. 5A, system 500 includes an eye tracker module 506, a drive module 510, and a video processing unit 508. Eye tracker module 506 is coupled with drive module 510 and video processing unit 508, and all are mounted onto vehicle 504. Vehicle 504 is operated by a driver 502.

Eye tracker module 506 comprises components including a camera module, a beam splitter, light sources, a display module, and a collimating optical assembly (all not shown) similar to system 100 of FIG. 1. The functionality of these units is analogous to the corresponding units with reference to system 100. Generally, eye tracker module 506 emits illuminating light beams and a display light beam toward the eye of driver 502, thereby illuminating the eye and displaying an image to driver 502. The image displayed may include different features or instructions associated with the road or the driving process, and allow driver 502 to select an element by activating a confirmation mechanism.

Since the head position of driver 502 is not constrained to a limited area, the position of the eye can be in a wide possible range within vehicle 504. According to one aspect of the disclosed technique, drive module 510 directs eye tracker module 506 toward the general location of the eye. This direction may be determined according to a head-mounted MPS or according to an off-user camera.

According to another aspect of the disclosed technique, there exists a plurality of eye tracker modules 506 that cover the entire area in which the head of the driver can move. Furthermore, there also exists a unit which determines which eye tracker module 506 to select for operation at any given time.

According to a further aspect of the disclosed technique, video processing unit 508 includes a high resolution detector (e.g. a CMOS imager). Such a high resolution detector, coupled with wide angle optics, covers a large field of view. It is noted that these aspects of the disclosed technique are not mutually exclusive. For example, a high resolution detector may be used together with a drive module 510, in order to improve accuracy.

Video processing unit 508 receives an image of the eye of driver 502 from eye tracker module 506. Video processing unit 508 analyzes the image of the eye and determines the line of sight of driver 502. Video processing unit 508 controls images to be displayed to driver 502 according to the line of sight. Video processing unit 508 may also analyze the image of the eye to determine a physiological state of driver 502. When certain physiological conditions are detected, video processing unit 508 can initiate a response accordingly, as described above in conjunction with the system 100.

Reference is now made to FIG. 5B, which is a schematic front-view illustration of system 500 (FIG. 5A). It is noted that eye tracker module 506 is mounted at a convenient location within vehicle 504, facing the user.

It is further noted that the light beams are not reflected off the surface of a lens (such as a visor), as in previous embodiments of the disclosed technique, but rather there is a direct path between the light beams and the eye of driver 502.

Figure 6:
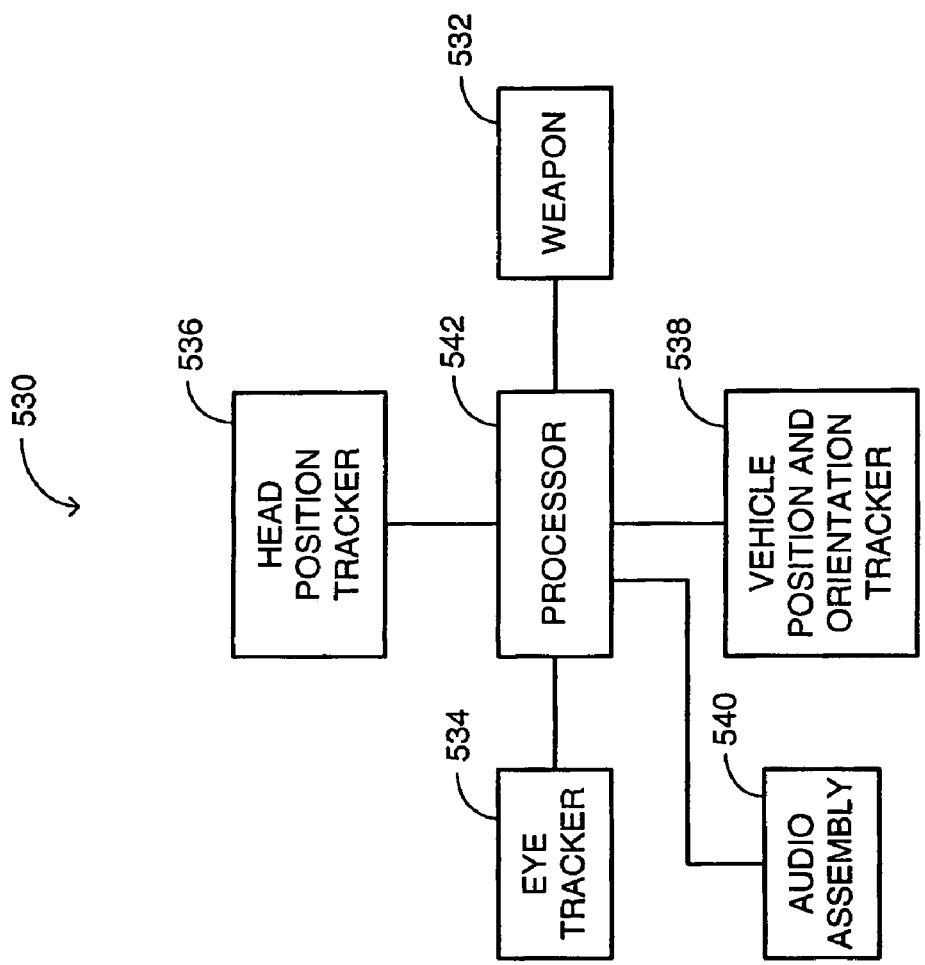
FIG. 6 is a schematic illustration of a system constructed and operative in accordance with a further embodiment of the disclosed technique, to direct a weapon toward a target.

Reference is now made to FIG. 6, which is a schematic illustration of a system, generally referenced 530, constructed and operative in accordance with a further embodiment of the disclosed technique, the system being employed to direct a weapon, generally referenced 532, toward a target. System 530 includes an eye tracker 534, a head position tracker 536, a vehicle position and orientation tracker 538, an audio assembly 540 and a processor 542. Weapon 532, eye tracker 534, head position tracker 536, vehicle position and orientation tracker 538 and audio assembly 540 are coupled with processor 542.

Weapon 532 includes a moving mechanism (not shown), such as an electric actuator, hydraulic actuator, pneumatic actuator, piezoelectric actuator, and the like. Processor 542 aims weapon 532 toward the target, according to data received from eye tracker 534, head position tracker 536 and vehicle position and orientation tracker 538, by employing the moving mechanism. Processor 542 directs audio assembly 540 to sound audible signals to a user (not shown) indicating predetermined states or operation modes of weapon 532.

It is noted that processor 542 may further be coupled with additional systems (not shown) which confirm the identity of the target based on measured and detected characteristics thereof such as material analysis (e.g., if the target is made of metal), shape analysis (e.g., based on shape oriented image processing), activity analysis (e.g., detecting transmissions originating from the target), and the like.

It will be appreciated by persons skilled in the art that the disclosed technique is not limited to what has been particularly shown and described hereinabove. Rather the scope of the disclosed technique is defined only by the claims, which follow.

The invention claimed is:

1. System for tracking the eye of a user, the system comprising:
    an image detector, directed at said eye, for detecting an eye image of at least said eye;
    at least one pupil-illuminating light source, each said at least one pupil-illuminating light source emitting a respective pupil-illuminating light beam, each said pupil-illuminating light beam having at least a portion being directed at the pupil of said eye, the portion being aligned with the optical axis of said image detector and at least partially illuminating the pupil of said eye;
    at least one reference light source that differs from said pupil-illuminating light source, each said at least one reference light source emitting a respective reference light beam, for illuminating a portion of the face of said user; and
    an imaging processor, coupled with said image detector, for analyzing said eye image, wherein at least a portion of each of said at least one pupil-illuminating light beam is reflected towards said image detector, thereby indicating a pupil region in said eye image, said pupil region being associated with said pupil, wherein at least a portion of each of said at least one reference light beam is reflected towards said image detector, thereby indicating at least one reference region in said eye image, each said reference region being associated with a recognizable portion of the face, wherein said imaging processor identifies said pupil region and at least one of said at least one reference region, and wherein said imaging processor determines the line of sight of said user according to said pupil region and according to at least one of said at least one reference region.

2. The system according to claim 1, wherein said imaging processor determines said line of sight according to the coordinates of the center of said pupil region.

3. The system according to claim 1, further comprising an optical relay assembly, wherein said optical relay assembly receives at least one selected light beam of said at least one pupil-illuminating light beam and said at least one reference light beam, and wherein said optical relay assembly directs at least a portion of said at least one selected light beam toward said eye.

4. The system according to claim 3, wherein said imaging processor controls said at least selected pupil-illuminating light source to produce said respective pupil-illuminating light beam, characterized by an increased intensity, when said intensity of ambient light increases, wherein said imaging processor controls said at least selected pupil-illuminating light source to produce said respective pupil-illuminating light beam, characterized by a decreased intensity, when said intensity of ambient light decreases, wherein said imaging processor identifies said pupil region as a brighter region in said eye image, when said intensity of ambient light increases, and wherein said imaging processor identifies said pupil region as a darker region in said eye image, when said intensity of ambient light decreases.

5. The system according to claim 1, further comprising at least one ambient light detector, for determining the intensity of ambient light in said eye image, wherein said imaging processor is further coupled with at least one of said at least one pupil-illuminating light source, and wherein said imaging processor controls at least a selected one of said at least one pupil-illuminating light source to produce said respective pupil-illuminating light beam, characterized according to said intensity of ambient light.

6. The system according to claim 1, wherein said imaging processor is further coupled with at least one selected light source of said at least one pupil-illuminating light source and said reference light source, and wherein said imaging processor controls said at least one selected light source according to said eye image.

7. The system according to claim 1, further comprising a beam splitter, wherein said beam splitter receives said pupil-illuminating light beam from said pupil-illuminating light source, wherein said beam splitter reflects at least a portion of said pupil-illuminating light beam toward said eye, and wherein said beam splitter transmits at least a portion of said eye image toward said image detector.

8. The system according to claim 1, further being mounted on a helmet.

9. The system according to claim 8, further comprising a helmet visor, wherein said helmet visor receives at least one selected light beam of said at least one pupil-illuminating light beam and said at least one reference light beam, and wherein said helmet visor at least partially reflects said at least one selected light beam toward said eye of said user.

10. The system according to claim 9, wherein said helmet visor at least partially transmits light from a scene, thereby allowing said user to view said scene.

11. The system according to claim 10, wherein said imaging processor selects a target from said scene according to said line of sight.

12. The system according to claim 11, further comprising at least one display light source, each said at least one display light source emitting a respective display light beam, each said display light beam carrying at least a portion of a display image, wherein said target is outside the field of display of said display image.

13. The system according to claim 9, wherein the shape of said visor is selected from the list consisting of:

spherical;

aspherical; and planar.

14. The system according to claim 1, further comprising at least one display light source, each said at least one display light source emitting a respective display light beam, each said display light beam carrying at least a portion of a display image.

15. The system according to claim 14, wherein said at least one display light source displays a target marking respective of a selected target, around said selected target, and wherein a weapon system is actuated when said target marking substantially matches said line of sight.

16. The system according to claim 14, wherein said at least one display light source further projects at least one stimulated light beam toward said eye, and wherein said imaging processor further analyzes the movement of said eye in response to said at least one stimulating light beam, thereby examining user reflexes.

17. The system according to claim 14, wherein said imaging processor registers a logical display element from said display image with the field of view of said user.

18. The system according to claim 14, wherein said display image is collimated.

19. The system according to claim 18, further comprising a collimator, for collimating said at least one display light beam.

20. The system according to claim 1, said imaging processor being further coupled with at least one display light source, wherein said imaging processor controls said at least one display light source to produce a display image according to said eye image.

21. The system according to claim 14, wherein at least a portion of at least one of said reference light sources is aligned with at least a portion of the optical axis of said display light source.

22. The system according to claim 1, wherein said recognizable portion of the face is the cornea.

23. The system according to claim 1, wherein said recognizable portion of the face is the eyelids.

24. The system according to claim 1, wherein said imaging processor further determines a physiological state of said user according to said eye image.

25. The system according to claim 24, wherein said imaging processor further determines said physiological state by comparing said eye image with a reference eye model, thereby detecting anomalies in said eye image.

26. The system according to claim 24, wherein said imaging processor further statistically analyzes said eye image, thereby determining temporal features of said eye.

27. The system according to claim 24, wherein said imaging processor further statistically analyzes said eye image, thereby determining temporal features of said eye, and
wherein said imaging processor further compares said temporal features with respective features associated with a reference eye model, thereby detecting anomalies in said eye.

28. The system according to claim 24, wherein said physiological state is selected from the list consisting of:
fatigue;
loss of consciousness;
cross-eye;
astigmatism;
eye damage; and
vertigo.

29. The system according to claim 24, wherein said imaging processor further initiates an alarm signal according to said physiological state.

30. The system according to claim 1, further comprising a stimulus light source, wherein said stimulus light source projects at least one stimulating light beam toward said eye, and
wherein said imaging processor further analyzes the movement of said eye in response to said at least one stimulating light beam, thereby examining user reflexes.

31. The system according to claim 1, wherein at least a selected one of said reference light beams is collimated.

32. The system according to claim 31, further comprising a collimator, for collimating said selected reference light beam.

33. The system according to claim 32, further comprising at least one display light source, each said at least one display light source emitting a respective display light beam, each said at least one display light beam carrying at least a portion of a display image,
wherein said collimator further collimates at least one of said at least one display light beam.

34. Method for tracking the eye of a user, the method comprising the procedures of:
emitting at least one pupil-illuminating light beam, each said at least one pupil-illuminating light beam having at least a portion being directed at the eye, the portion being aligned with an optical axis of an image detector and at least partially illuminating the pupil of said eye;
emitting at least one reference light beam differing from said pupil-illuminating light beam, for illuminating a portion of the face of said user;
detecting an eye image of at least said eye, around the optical axis of the image detector;
identifying in said eye image a pupil region and at least one reference region associated with a recognizable portion of the face; and
determining the line of sight of said user according to said pupil region and according to at least one of said at least one reference region,
wherein at least a portion of said at least one pupil-illuminating light beam indicates said pupil region in said eye image,
wherein at least a portion of each of said at least one reference light beam indicates said at least one reference region in said eye image, and
wherein said line of sight is determined according to said pupil region and according to at least one of said at least one reference region.

35. The method according to claim 34, wherein said line of sight is further determined according to the coordinates of the center of said pupil region.

36. The method according to claim 34, further comprising the procedure of emitting at least one display light beam, each said display light beam carrying at least a portion of a display image.

37. The method according to claim 36, further comprising the procedure of collimating said at least one display light beam.

38. The method according to claim 36, further comprising the procedure of controlling at least said display light beam according to said line of sight, after said procedure of determining said line of sight.

39. The method according to claim 34, further comprising the preliminary procedure of detecting ambient light,
wherein at least a selected one of said at least one pupil-illuminating light beam and said at least one reference light beam is produced according to said detected ambient light.

40. The method according to claim 34, wherein said recognizable portion of the face is the cornea.

41. The method according to claim 34, wherein said recognizable portion of the face is the eyelids.

42. The method according to claim 34, further comprising the procedure of directing at least one of said at least one pupil-illuminating light beam toward said eye, performed after said procedure of emitting said at least one pupil-illuminating light beam.

43. The method according to claim 42, further comprising the procedure of directing at least a portion of said pupil-illuminating light beam toward an image detector, performed after said procedure of directing said at least one of said at least one pupil-illuminating light beam toward said eye.

44. The method according to claim 34, further comprising the procedure of directing at least one of said at least one reference light beam toward the face of said user, performed after said procedure of emitting said at least one reference light beam.

45. The method according to claim 44, further comprising the procedure of directing at least a portion of said reference light beam toward an image detector, performed after said procedure of directing at least one of said at least one reference light beam toward said face.

46. The method according to claim 34, further comprising the procedure of collimating said at least one reference light beam.

47. The method according to claim 34, further comprising the procedure of determining a physiological state of said user according to said eye image.

48. The method according to claim 47, wherein said physiological state is determined by comparing said eye image with a reference eye model, thereby detecting anomalies in said eye image.

49. The method according to claim 47, further comprising the procedures of:
statistically analyzing said eye image, thereby determining statistical features of said eye; and comparing said statistical features with respective features associated with a reference eye model, thereby determining anomalies in said eye, wherein said physiological state is further determined according to said anomalies.

50. The method according to claim 34, further comprising the procedure of statistically analyzing said eye image, thereby determining statistical features of said eye.

51. The method according to claim 34, further comprising the procedures of:

identifying a target along said determined line of sight;

prompting user confirmation for target acquisition;

receiving user confirmation of said target; and directing a weapon toward said target.

52. System for directing a weapon toward a target, the system comprising:

an eye tracker for tracking the eye of a user;

a head position tracker for monitoring at least the position of the head of said user;

a vehicle position and orientation tracker for monitoring the position and orientation of a vehicle; and a processor coupled with said eye tracker, said head position tracker and with said vehicle position and orientation tracker, wherein said eye tracker comprises:

an image detector directed at said eye, for detecting an eye image of at least said eye;

at least one pupil-illuminating light source, each said at least one pupil-illuminating light source emitting a respective pupil-illuminating light beam, at least a portion of each said pupil-illuminating light beam being aligned with at least a portion of the optical axis of said image detector, each said pupil-illuminating light beam at least partially illuminating the pupil of said eye;

at least one reference light source, each said at least one reference light source emitting a respective reference light beam, for illuminating a portion of the face of said user; and an imaging processor, coupled with said image detector, for analyzing said eye image, wherein at least a portion of each of said at least one pupil-illuminating light beam is reflected towards said image detector, thereby indicating a pupil region in said eye image, said pupil region being associated with said pupil, wherein at least a portion of each of said at least one reference light beam is reflected towards said image detector, thereby indicating at least one reference region in said eye image, each said reference region being associated with a recognizable portion of said face, wherein said imaging processor identifies said pupil region and at least one of said at least one reference region, wherein said imaging processor determines the line of sight of said user according to said pupil region and according to at least one of said at least one reference region, and wherein said processor directs said weapon toward said target according to said line of sight, said at least position of said head and according to said position and orientation of said vehicle.

53. The system according to claim 52, further comprising an audio assembly coupled with said processor, said audio assembly sounding audible signals to said user indicating predetermined states or operation modes of said weapon.

* * * * *